United States Patent
Gopalan et al.

(10) Patent No.: US 9,625,572 B2
(45) Date of Patent: Apr. 18, 2017

(54) METHOD AND APPARATUS FOR SIGNAL PATH EQUALIZATION IN A SCANNING ACOUSTIC MICROSCOPE

(75) Inventors: Sriram Gopalan, Burke, VA (US); James C. P. McKeon, Woodbridge, VA (US)

(73) Assignee: Sonix, Inc., Springfield, VA (US)

(*) Notice: Subject to any disclaimer, the term of this patent is extended or adjusted under 35 U.S.C. 154(b) by 1023 days.

(21) Appl. No.: 13/459,667

(22) Filed: Apr. 30, 2012

(65) Prior Publication Data

US 2013/0128690 A1 May 23, 2013

Related U.S. Application Data

(60) Provisional application No. 61/561,438, filed on Nov. 18, 2011.

(51) Int. Cl.

| | |
|---|---|
| *G01S 7/52* | (2006.01) |
| *G01S 15/89* | (2006.01) |
| *B82Y 35/00* | (2011.01) |
| *G01Q 30/06* | (2010.01) |
| *G01N 29/06* | (2006.01) |
| *G01N 29/44* | (2006.01) |

(52) U.S. Cl.
CPC ............ *G01S 7/5205* (2013.01); *B82Y 35/00* (2013.01); *G01N 29/0681* (2013.01); *G01N 29/44* (2013.01); *G01Q 30/06* (2013.01); *G01S 15/8938* (2013.01)

(58) Field of Classification Search
CPC ....... A61B 8/14; G01H 17/00; B65H 2553/30
USPC ........................................................ 702/103
See application file for complete search history.

(56) References Cited

U.S. PATENT DOCUMENTS

| | | |
|---|---|---|
| 4,028,933 A | 6/1977 | Lemons et al. |
| 4,030,342 A | 6/1977 | Bond et al. |
| 4,518,992 A | 5/1985 | Kessler et al. |

(Continued)

FOREIGN PATENT DOCUMENTS

| | | |
|---|---|---|
| CA | 1029462 | 4/1978 |
| DE | 2504988 | 1/1976 |

(Continued)

OTHER PUBLICATIONS

PCT Search Report and Written Opinion, PCT/US2012/035783, Nov. 7, 2012.

*Primary Examiner* — Edward Raymond
(74) *Attorney, Agent, or Firm* — Leveque IP Law, P.C.

(57) ABSTRACT

A scanning acoustic microscope includes a signal processor and one or more signal paths. In operation, each signal path couples an ultrasonic transducer to the signal processor that processes signals received from the signal paths to produce an ultrasonic scan image. Each signal path has a response characteristic that includes a response characteristic of the ultrasonic transducer. In order to compensate for variations between the signal paths or variations between different transducers in the same signal path, at least one of the signal paths includes a signal path equalizer. The equalizer may be responsive to a set of equalization coefficients. The coefficients are selected such that the response characteristic of the signal path including the equalizer more closely matches a reference characteristic response. The equalizer may operate on a transmitted or received signal or be used to generate an ultrasonic pulse.

37 Claims, 9 Drawing Sheets

(56) References Cited

U.S. PATENT DOCUMENTS

| | | | |
|---|---|---|---|
| 4,980,865 A | 12/1990 | Ishibashi et al. | |
| 5,331,855 A | 7/1994 | Takashita | |
| 5,511,425 A | 4/1996 | Kleinert et al. | |
| 5,533,401 A | 7/1996 | Gilmore | |
| 5,553,499 A | 9/1996 | Hisata et al. | |
| 6,374,675 B1 | 4/2002 | DePetrillo | |
| 6,415,665 B1 * | 7/2002 | Gilmore | B29C 47/92 425/169 |
| 6,460,414 B1 | 10/2002 | Erickson et al. | |
| 6,813,926 B2 * | 11/2004 | Dunning et al. | 73/7 |
| 6,875,178 B2 | 4/2005 | Phelps et al. | |
| 6,880,387 B2 | 4/2005 | Kessler et al. | |
| 6,895,820 B2 | 5/2005 | Oravecz et al. | |
| 7,000,475 B2 | 2/2006 | Oravecz et al. | |
| 7,013,732 B2 | 3/2006 | McKeon | |
| 7,302,070 B2 * | 11/2007 | Blamey et al. | 381/318 |
| 8,744,793 B2 * | 6/2014 | McKeon | 702/103 |
| 2003/0023393 A1 | 1/2003 | Oravecz | |
| 2004/0220463 A1 | 11/2004 | Satoh | |
| 2005/0033167 A1 | 2/2005 | Trucco et al. | |
| 2005/0229707 A1 | 10/2005 | Oravecz et al. | |
| 2006/0272419 A1 | 12/2006 | Maris et al. | |
| 2009/0095086 A1 | 4/2009 | Kessler et al. | |
| 2010/0174190 A1 | 7/2010 | Hancock et al. | |

FOREIGN PATENT DOCUMENTS

| | | |
|---|---|---|
| DE | 202006020868 | 9/2010 |
| DE | 202006020870 | 9/2010 |
| DE | 202006020867 | 10/2010 |
| DE | 202006020869 | 10/2010 |
| DE | 102006005449 | 11/2010 |
| DE | 102006005448 | 2/2011 |
| EP | 1049071 | 11/2000 |
| JP | 58-106453 | 6/1983 |
| JP | 58-039942 | 8/1983 |
| JP | 59-044582 | 3/1984 |
| JP | 60-098359 | 6/1985 |
| JP | 62-249054 | 10/1987 |
| WO | WO 01/86281 | 11/2001 |

* cited by examiner

METHOD AND APPARATUS FOR SIGNAL PATH EQUALIZATION IN A SCANNING ACOUSTIC MICROSCOPE

PRIORITY CLAIM

This application claims the benefit of U.S. Provisional Patent Application 61/561,438 filed 18 Nov., 2011 and titled 'Equalization of Signal Paths in a Multi-Transducer Scanning Acoustic Microscope', which is hereby incorporated by reference herein.

BACKGROUND

Scanning Acoustic Microscopy (SAM) is a non-destructive method used to detect cracks, voids, and de-laminations occurring in the surface/sub-surface of different kinds of objects under test. One application of Scanning Acoustic Microscopy is defect detection in semi-conductor packages. Examples of semi-conductor packages include wire bond/ribbon bond packages, flip chip packages, tape automated bond packages, ball grid array packages, chip scale packages, printed circuit boards and bonded wafers (including blank, patterned, MEMS, and 3D Interconnect wafers). Apart from defect detection, SAM is also helpful in metrology applications such as measurement of material (bond layer/wafer) thickness, trench depth measurement and evaluation of wafer pair alignment post bonding.

In a pulse echo mode of imaging, an ultrasonic transducer generates an ultrasonic pulse (coupled through water) and, as the ultrasound travels through the object under test, a portion of the signal is reflected. The reflection depends on changes in acoustic impedance in the object. The reflected signal is converted back into an electrical signal and, in turn, into a pixel value for the location being tested. The conversion uses a signal path typically including a transducer, a pulser/receiver, and an analog-to-digital (A-D) conversion board. Once the pixel value is obtained for a single location with Cartesian coordinates (x, y), the motion controller moves the transducer to the next pixel coordinate, based on the scan resolution. Thus, a raster scan is performed on the entire region of interest to obtain a SAM image of the sample.

The throughput of the SAM system is limited by the speed of the motors that move the transducer across the surface of the object under test (the Scan-X and the Scan-Y axes, for example) and the repetition rate of the pulser/receiver. In order to minimize the duration of a scan, it is desirable to increase the throughput of SAM systems. SAM systems may be used both in the front end (wafer) of a production line and at the back end (package) of the line.

SAM systems are available in both manual and automated modes. Manual systems require the user to manually load and unload the samples (packages/wafers) before and after the scan. In an automated wafer inspection system, the cassettes or Front Opening Unified Pods (FOUP's) of wafers are placed in the loading stations and a robot transfers the wafers into a scanning chamber. Once scanning is completed, the robot removes the wafers from the scanning chamber, moves them to a drying chamber and then back into the appropriate wafer slot on the cassette/FOUP in the loading station. In automated package inspection systems, the Joint Electron Devices Engineering Council (JEDEC) standard trays populated with the samples are placed in the loading station. The samples are picked up and placed in the scanning station row by row. After scanning and drying is completed, the samples are picked up and placed back into the JEDEC trays. The tray is then transferred to an unloading station on a conveyor belt.

The throughput of the system is generally defined in terms of the time taken to inspect one object from the cassette/FOUP/tray (from inputting a dry object to outputting a dry object). The total time includes time for scanning, data acquisition, analysis, and handling. Optimizing any, or all, of these parameters will improve throughput. For example, designing the system to perform operations in parallel, rather than in series, minimizes the impact of the handling and analysis times on the overall throughput. Automated systems, where three wafers are in the system at the same time (i.e. one wafer at each of the pre-aligner, scan station, and dryer station), have greatly reduced the handling time per wafer. Analyzing one wafer while the next wafer is being scanned reduces the analysis impact on throughput to a negligible amount. However, the dominant factor affecting throughput is the scan time itself. Optimizing the data transfer time for each scan line of data does have an impact on the throughput since the scan can run continuously rather than having to wait briefly at the end of each scan line for data transfer. However, even this improvement does not meet the industry requirements for throughput.

Previous work has focused on three methods for improving the scan time: multiple scan stations (i.e. multiple sets of raster scanner, transducer, and sample holder), multiple sample holders (one raster scanner and transducer combination moves over multiple sample holders), or multiple transducers (one raster scanner moves multiple transducers over one sample holder).

The first option (multiple scan stations) allows for completely separate motion over different samples at the same time. However, it requires multiple complete scanning stations, which increase the complexity and footprint of the system. This is a major consideration on a production floor, where space is at a premium. Also, if one scan station in the system has a problem, the whole system has to go off-line to be serviced. This has a major impact on throughput.

The second option (multiple holders) allows for one scan motion over multiple samples, which requires less duplication of scan station components and could allow for greater scan speeds since there is more distance over which acceleration can be applied. However, this option also requires an increase in system footprint. Further, if one sample holder has a problem, the whole system has to go off-line to be serviced.

The third option (multiple transducers) requires some added complexity for the acquisition paths, but the system footprint would be the same as for a single transducer—single scan station system. Also, if a problem occurs on this type of system, only that one scan station is affected. Other scan stations (systems) will keep running. Also, the multiple transducer (multi-transducer) approach, using N transducers, can potentially reduce the scan time by a factor of N.

The main challenge in the multi-transducer approach is the inherent variation in the performance of one transducer compared to another. Though the transducers may be within the required specification, there may be slight focal length differences, or variation in the strength of the signal of interest, the waveform shape of the signal, or the phase of the signal, for example. These variations in transducers can result in variations in the scanned image. The multi-transducer approach requires an image to be pieced together from multiple transducer data and transducer variations can result in an image with a patchwork appearance. This can also negatively impact analysis results for the sample. Previous work in the multi-transducer approach has allowed for independent focusing of each transducer to account for the differences in focal length between transducers. However, no prior work has addressed the signal strength and shape/phase variations.

In a SAM system, the characteristic of the signal path is dependent, in part, on the response of the one or more transducers in the path. If a transducer in the signal path is replaced, because of failure or other reason, the characteristic of the signal path is changed. This makes it more difficult to compare scans made using different transducers or using different SAM systems. In addition, the time-gates of the system may need to be checked and possibly repositioned, since the phase response of the new transducer may be different.

BRIEF DESCRIPTION OF THE FIGURES

The accompanying figures, in which like reference numerals refer to identical or functionally similar elements throughout the separate views and which together with the detailed description below are incorporated in and form part of the specification, serve to further illustrate various embodiments and to explain various principles and advantages all in accordance with the present invention.

Skilled artisans will appreciate that elements in the figures are illustrated for simplicity and clarity and have not necessarily been drawn to scale. For example, the dimension of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method processes and apparatus components related to the equalization of signal paths in a multi-transducer scanning acoustic microscope. Accordingly, the apparatus components and method processes have been represented, where appropriate, by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

It will be appreciated that embodiments of the invention described herein may comprise one or more conventional processors and unique stored program instructions that control the one or more processors to implement, in conjunction with certain non-processor circuits, some, most, or all of the functions for the equalization of signal paths in a multi-transducer scanning acoustic microscope described herein. The non-processor circuits may include, but are not limited to, transducers, analog filters, digital filters, amplifiers, signal drivers, clock circuits, power source circuits, and user input devices. As such, these functions may be interpreted as a method to perform the equalization of signal paths in a multi-transducer scanning acoustic microscope. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used. Thus, methods and means for these functions have been described herein. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The present invention relates to a scanning acoustic microscope that includes a signal processor and one or more signal paths. The signal processor is operable to process signals received from the signal paths to produce an ultrasonic scan image.

Each signal path is operable to couple one or more ultrasonic transducers to the signal processor. Each signal path has a response characteristic that includes a response characteristic of at least one ultrasonic transducer.

In order to compensate for variations between the signal paths, or variation between different transducers used in a single signal path, at least one signal path includes a signal path equalizer that is responsive to a set of equalization coefficients. The equalization coefficients are selected such that the response characteristic of the equalized signal path more closely matches a reference characteristic response.

Typically, each signal path includes a signal generator, transducer, a pulser/receiver and an analog-to-digital (A-D) conversion board. Using different signal paths for each transducer in a multi-transducer system enables different equalization coefficients (which may determine gains and/or phases) to be set for each signal path, and thereby account for strength differences between the one or more transducers in the path. In one embodiment of the invention, these equalization coefficients are stored in a recipe (a description of the process) for inspecting the samples. In addition, different focus positions may be saved, so that the focus and strength variations may be accounted for automatically. In one implementation, the values in the recipe are stored as offsets from a main/reference value. For example, in a four transducer system, the main gain value and focus position would be set by transducer 1. Offsets from these values are stored for each of the other three transducers. A further benefit of this approach is that it allows the offsets to be in a configuration file, rather than a recipe, so that any recipe from any system could be loaded and then the offsets required for all N transducers would be applied to get the desired focus and strength results. In a further example, the gain value of each transducer, together with an identifier of the transducer (such as a serial number), may be stored in a system memory or in a remote memory. When the system is setup, the serial number of the transducer being used is entered at a user interface to enable the SAM to retrieve and use the correct equalizer value.

Time gates may used to separate reflections from different surfaces, since the reflections have different propagation times. Wider time gates may be used when the object under test has only a single interface and when there is no need to check for phase inversions caused by defects. In this situation, focus and gain adjustments for each transducer may be sufficient to produce improved images for analysis. However, variations in the signal shape and/or phase between transducers can have a negative impact on the resulting image when inspecting multiple interfaces (which requires the use of narrow time gates) or when phase inversion is a desired analysis criterion. For example, if narrow time gates are used and there is a variation in the signal shape, then one portion of the image could be from a different depth in the sample than another.

Figure 1:
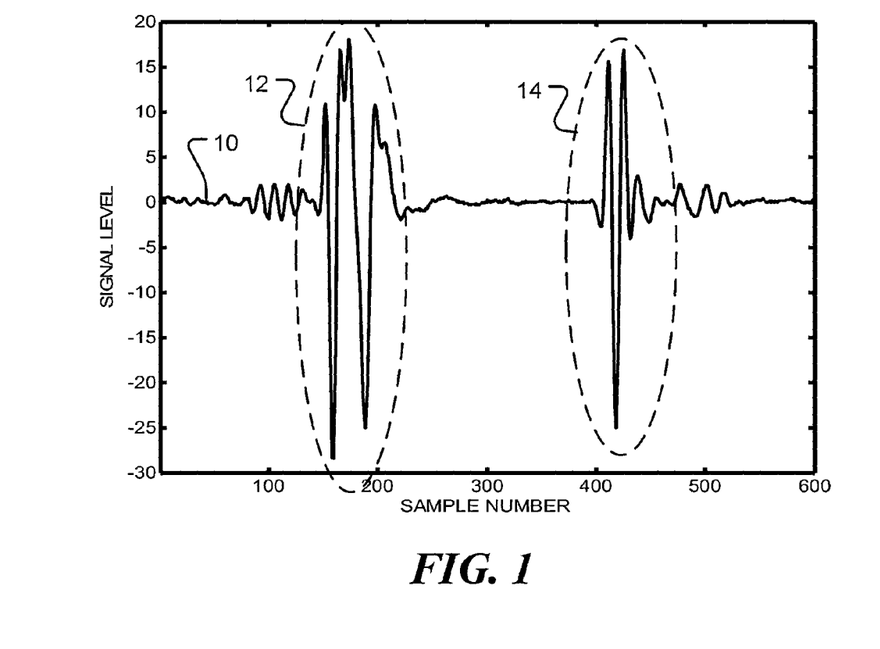
FIG. 1 is an example waveform received from a first transducer.
Figure 2:
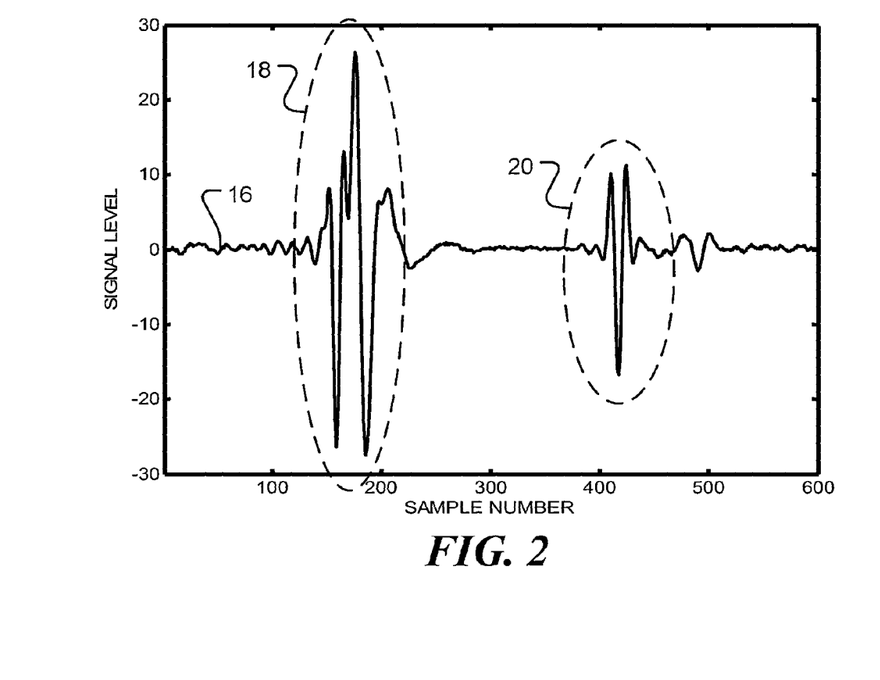
FIG. 2 is an example waveform received from a second transducer.

FIG. 1 and FIG. 2 show example waveforms received from two different transducers. In these examples, the transducers both have an 8 mm focal length with an operating frequency of 110 MHz. The transducers produce waveforms with different shapes, even though the transducers are of the same type.

Referring to FIG. 1, the waveform 10 is plotted as a function of time (measured in samples). In this example, the signal level is plotted as a percentage of full scale. This is referred to as an A-scan. The region 12 corresponds to a reflection from the top surface of the wafer while the region 14 corresponds to the reflection from a subsurface of the wafer. Similarly, in FIG. 2, the waveform 16 is plotted as a function of time (in samples). The region 18 corresponds to a reflection from the top surface of the wafer while the region 20 corresponds to the reflection from a subsurface of the wafer.

Comparison of the regions 12 and 18 in FIGS. 1 and 2 reveals a variation in the shape of the signal from the top surface of the wafer between the two transducers. This variation can adversely affect the triggering of subsequent time gates. The variation can also cause a difference in brightness between the images when imaging the surface/near surface of the wafer.

Similarly, comparison of the regions 14 and 20 in FIGS. 1 and 2 reveals a difference in the intensity of signal at the sub surface received from the two transducers. This difference will cause brightness variation in the images of the samples, as shown in FIGS. 3-5.

Figure 3:
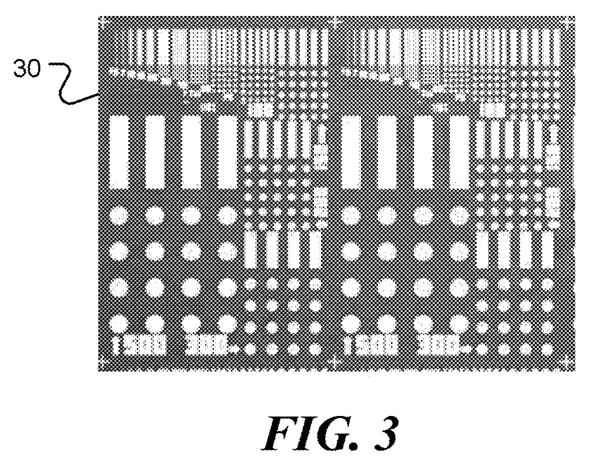
FIG. 3 is an example scanning acoustic microscope (SAM) image of a calibration wafer from the first transducer.
Figure 4:
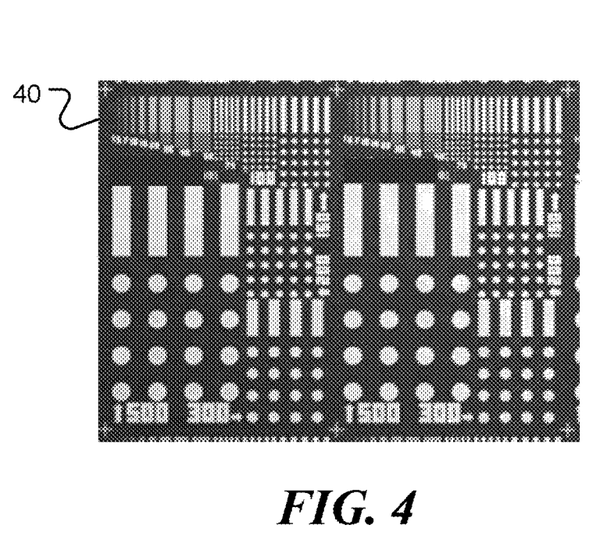
FIG. 4 is an example scanning acoustic microscope (SAM) image of a calibration wafer from the second transducer.

FIG. 3 shows a SAM image of the wafer as produced by the first transducer, while FIG. 4 shows a SAM image of the wafer as produced by the second transducer.

Figure 5:
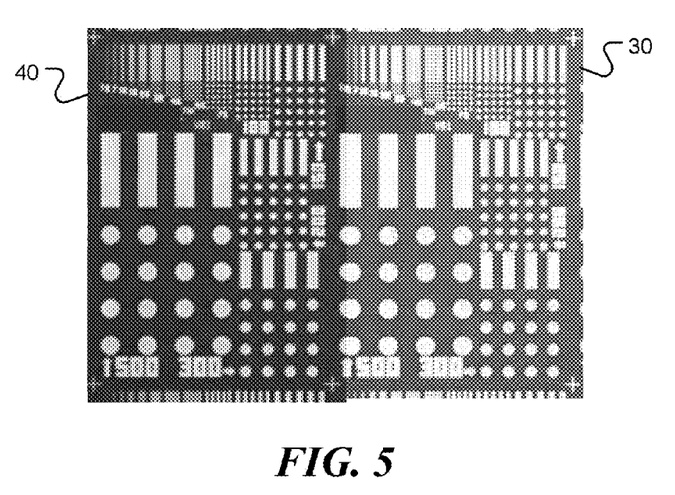
FIG. 5 is an example scanning acoustic microscope (SAM) image of a calibration wafer from a multi-transducer scanner.

FIG. 5 shows the corresponding SAM image that would be obtained with a multi-transducer SAM that uses the first and second transducers. In FIG. 5, the first transducer was used to produce the image 30 of the right hand device (device 2), and the second transducer was used to produce the image 40 of the left hand device (device 1).

The variation in the brightness of the image is clearly visible. This variation is mainly due to the variation in the waveform shape shown in FIGS. 1 and 2. The variation in the brightness of the images may lead to erroneous analysis results.

As mentioned above, gain equalization, in which different gains are applied to different transducer acquisition paths, addresses the variation in signal strength (amplitude) but does not address the variation in the shape of the waveform. Advancements in the semiconductor industry lead to decreasing die/wafer thicknesses that, in turn, requires the use of narrower gates. Thus, it is desirable to match not only the signal strength, but also the signal shape. In one embodiment, equalization of the waveforms is achieved through the use of an equalization filter.

The variation in the shape of the waveform is dependent, at least in part, on the characteristic of the transducer. Different transducers may have different responses. Thus, if the transducer in a signal path is changed, the characteristic of the path is changed. This would require the positions of the time-gates to be checked and possibly readjusted. In one embodiment, the characteristic of each transducer is measured and equalization coefficients are determined for the transducer. The equalization coefficients may be chosen such that the equalized response matches a desired response. The desired response may be, for example, a response obtained by averaging over transducers of the same type. When a transducer is changed, the equalizer coefficients corresponding to the transducer are loaded into the equalizer of the path. This has the benefits of avoiding the need to check and adjust time-gates and also ensures that scans from different transducers have a consistent appearance. Thus, use of signal path equalizers is beneficial in SAM systems having a single signal path or multiple signal paths.

In one embodiment, the signal path equalizer is responsive to a set of equalization coefficients that are selected, dependent upon the ultrasonic transducer in the signal path, such that the response characteristic of the signal path more closely matches a reference characteristic response. A plurality of sets of equalizer coefficients, each set of equalizer coefficients corresponding to a particular ultrasonic transducer, may be stored in a memory. The memory may be a local memory of the SAM, or the SAM may include a network interface that is operable to link to a remote memory via a network.

Figure 6:
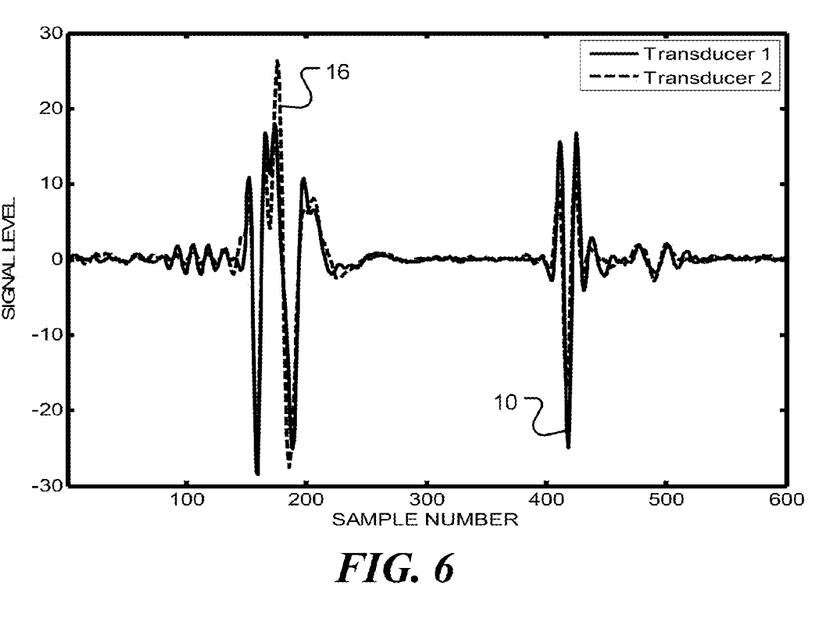
FIG. 6 shows a comparison between example waveforms received from first and second transducers.

One embodiment of a waveform equalizer uses frequency domain filtering, in which a frequency domain transfer function is applied to the frequency domain spectrum of the waveform and an inverse transform is applied to recover the equalized time domain signals. FIG. 6 shows example waveforms, 10 and 16, from two transducers before equalization is applied. Again, the waveforms are plotted as a function of time (measured in samples) and the level is shown as a percentage of full scale. The waveform from the first transducer is shown as a solid line, and the waveform from the second transducer is shown as a dashed line.

Figure 7:
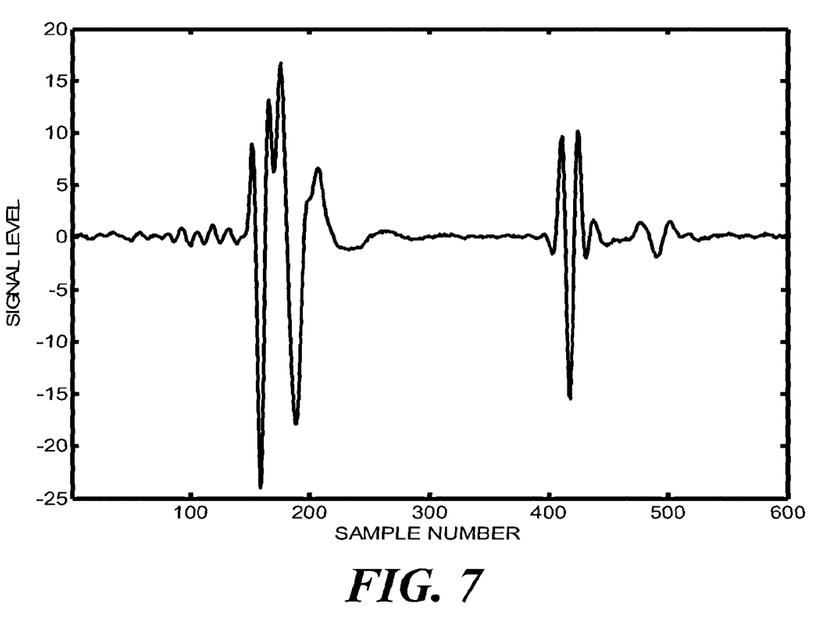
FIG. 7 is an example of a reference waveform, in accordance with some embodiments of the invention.

In one approach, a reference waveform for each model of transducer is created. FIG. 7 shows an example reference waveform 70 obtained by averaging numerous waveforms obtained from different transducers of the same type (in this case, 110 MHz 8 mm transducers). The average of NA-scan waveforms is calculated as $$A_{avg} = (A_{ASCANS\_1} + A_{ASCANS\_2} + A_{ASCANS\_3} \cdots + A_{ASCANS\_N})/N. \quad (1)$$

The time domain or frequency domain waveforms may be averaged. Using the reference waveform $A_{avg}$ in the frequency domain, transfer functions $H_{TF}$ for each transducer can be obtained as $$H_{TF\_1} = A_{avg}/A_{ASCANS\_1}$$

$$H_{TF\_2} = A_{avg}/A_{ASCANS\_2}$$

$$H_{TF\_3} = A_{avg}/A_{ASCANS\_3}$$

$$H_{TF\_N} = A_{avg}/A_{ASCANS\_N} \quad (2)$$

The transfer function will then be applied to each A-scan (obtained dynamically for each transducer) resulting in a set of A-scans for each transducer that should match the results that would have been obtained by the "reference" transducer. Thus, a different equalizer characteristic is used for each signal path, the characteristic corresponding to the response of that path. After equalization, the A-scans (in the frequency domain) are:

$$A_{EQ\_1} = H_{TF\_1} * A_{ASCAN\_1} = A_{avg}$$

$$A_{EQ\_2} = H_{TF\_2} * A_{ASCAN\_2} = A_{avg}$$

$$A_{EQ\_3} = H_{TF\_3} * A_{ASCAN\_3} = A_{avg}$$

$$A_{EQ\_N} = H_{TF\_N} * A_{ASCAN\_N} = A_{avg} \quad (3)$$

Figure 8:
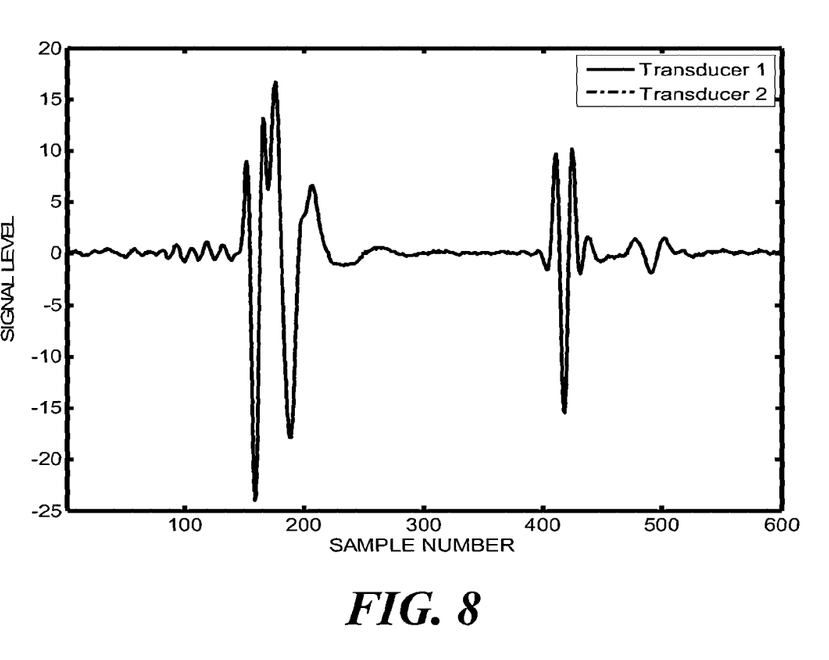
FIG. 8 shows examples of equalized waveforms from first and second transducers in accordance with some embodiments of the invention.

FIG. 8 shows the equalized A-scans, 80 and 82, for two transducers. The waveforms are closely matched to the reference waveform and virtually indistinguishable from one another.

In a SAM image, each pixel value is obtained from a time-gated region of a waveform received when a transducer is at a corresponding location relative to the object being scanned. Equalization is applied to each waveform at each location to enable an equalized image to be formed. In one embodiment, the equalization is applied in real-time as the waveforms are acquired. In a further embodiment, the equalization is applied during post-processing after a number of waveforms have been acquired.

Figure 9:
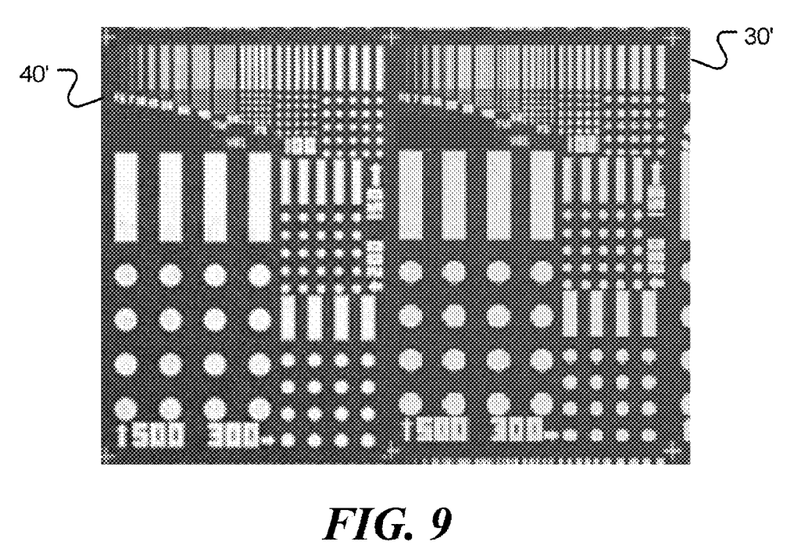
FIG. 9 is an example scanning acoustic microscope (SAM) image of a calibration wafer from a multi-transducer scanner having equalized signal paths in accordance with some embodiments of the invention.

FIG. 9 shows equalized SAM images, 30' and 40', from a multi-transducer SAM having two transducers. Application of the appropriate transfer function to the A-scans obtained at each pixel yields a similar waveform for all transducers at that pixel location. Referring to FIG. 9, it can be seen that the images 30' and 40' are closely matched.

It is noted that $$A_{ASCANS\_N} = TF_N * X_N, \quad (4)$$

where $X_N$ is the excitation waveform and $TF_N$ is the system response. Since the system is substantially linear, $$H_{TF\_N} * A_{ASCANS\_N} = H_{TF\_N} * (TF_N * X_N) = TF_N/(H_{TF\_N} * X_N), \quad (5)$$

where $(H_{TF\_N} * X_N)$ is an equalized excitation signal. Thus, the equalization may be applied to the excitation signal $X_N$ and/or to the response signal $A_{ASCANS\_N}$. Equalization of the excitation signal may be used to compensate for variations in a transmitting transducer, a receiving transducer, or a combination thereof. Similarly, equalization of the received (response) signal may be used to compensate for variations in a transmitting transducer, a receiving transducer, or a combination thereof.

A comparison of FIGS. 5 and 9 shows that, after equalization of the waveform, the device scanned by the first transducer is a little darker than the same image produced without equalization and the device scanned by the second transducer is a little brighter, resulting in an overall image that is better balanced.

Figure 10:
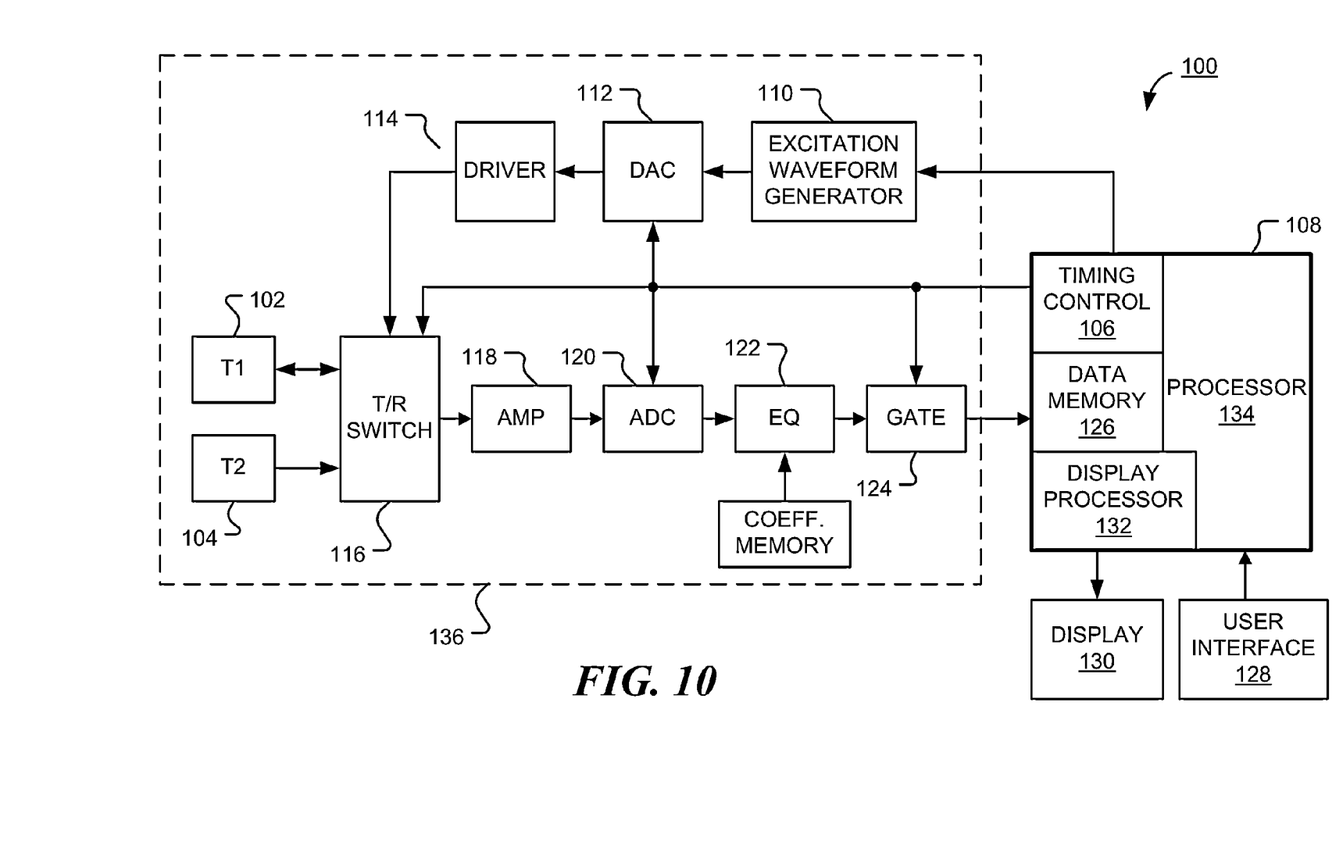
FIG. 10 is a block diagram of an exemplary scanning acoustic microscope (SAM) or ultrasound system in accordance with some embodiments of the invention.

FIG. 10 is a block diagram of an exemplary scanning acoustic microscope or ultrasound system 100 in accordance with some embodiments of the disclosure. In operation, a pulse of ultrasound generated from a first ultrasonic transducer (T1) 102 is reflected from, or transmitted through, an object to be imaged or otherwise tested. In a pulse-echo system, reflected ultrasound may be sensed by the first transducer 102 or by a second transducer (T2) 104. In a through transmission system, transmitted sound is sensed by the second transducer 104. A timing control module 106 of a computer 108 controls a waveform generator 110 to generate a digital waveform that is converted to an analog waveform by a digital-to-analog converter (DAC) 112. A driver 114 amplifies the analog signal. Transmitted and/or reflected ultrasound is sensed by the transducers 102 and/or 104. A transmit/receive (T/R) switch 116 is used to select whether the amplified signal is coupled to the transducer 102, or whether the signal generated by the transducer 102 in response to sensed ultrasound is passed to low-noise pre-amplifier 118. The pre-amplified sensed signals are passed to an analog to digital converter (ADC) 120, and then to a signal path equalizer level 122. A time gate 124 selects regions of digitized sensed signal corresponding to reflections from the object being imaged. In one embodiment, the digitized samples are stored in a data memory 126 of the computer 108 and may be processed by a signal processor 134. A selected portion of the digitized sensed signal may be sent to a display unit 130. The timing control module 106 synchronizes the timing of the various components of the system, including the DAC 112, the T/R switch 116, the level adjuster 120, the ADC 124 and the time gate 124.

The display 130 may be used to display graphical waveforms, a graphical user interface and other information, under the control of a display processor 132.

The elements shown in box 136 form a signal path. In the embodiment shown in FIG. 10, the signal path 136 includes the transmission path, by which an excitation waveform from excitation waveform generator 110 is converted to ultrasound. The signal path 136 also includes the reception or acquisition path, by which ultrasound received by the transducer is converted to a digitized signal.

In a further embodiment, the signal path may include only the transmission path or only the reception path.

Since the signal path is a substantially linear system, the signal path equalizer 122 may be located at other locations in the signal path. For example, it could be placed in the outgoing path before the DAC 112. In this example, the equalizer modifies the waveform to be generated. If the same waveform is generated repeatedly, as is common in scanning acoustic microscopes, the equalization need only be applied once, and may be applied before the scan begins. This may require less computation than equalizing each response. As a further example, the equalizer 122 could be placed after the time gate 124. This reduces the amount of computation required to apply the equalization, but may not be optimal if the equalization includes significant time or phase modification.

The signal path equalizer may be located at any position in the signal path. In one embodiment, the equalizer operates on a signal in the analog portion of the signal path and may comprise a level adjuster or analog filter, for example. In a further embodiment, the equalizer operates on sampled data in the signal path.

Operation of the signal path equalizer 122 is controlled by a set of equalization coefficients. The set of equalization coefficients may be stored in a coefficient memory 138.

Figure 11:
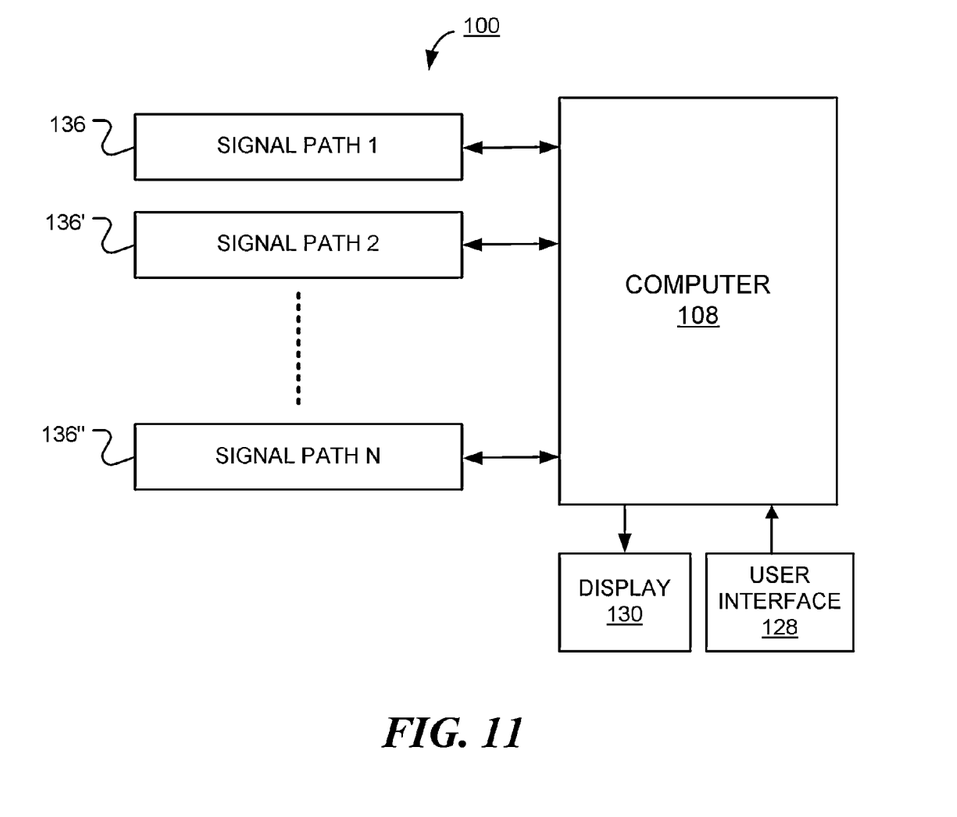
FIG. 11 is a block diagram of a scanning acoustic microscope (SAM) with multiple transducers in accordance with some embodiments of the invention.

Multiple sensing or transmitting transducers may be used, in which case the signal path 136 may be duplicated for each additional transducer. FIG. 11 is a block diagram of a scanning acoustic microscope with multiple transducers and multiple signal paths. Referring to FIG. 11, the scanning acoustic microscope 100 comprises a computer 108, multiple signal paths 136, 136' and 136", a display 130 and a user interface 128. Those of ordinary skill in the art will recognize that other components, such as transport mechanisms for moving the transducers and/or an object being scanned, are omitted for simplicity.

In one embodiment of the disclosure, all signal paths include equalizers. In a further embodiment, one signal path is used as a reference signal path and has no equalization. Equalization of the other signal paths is chosen to match the reference signal path.

Figure 12:
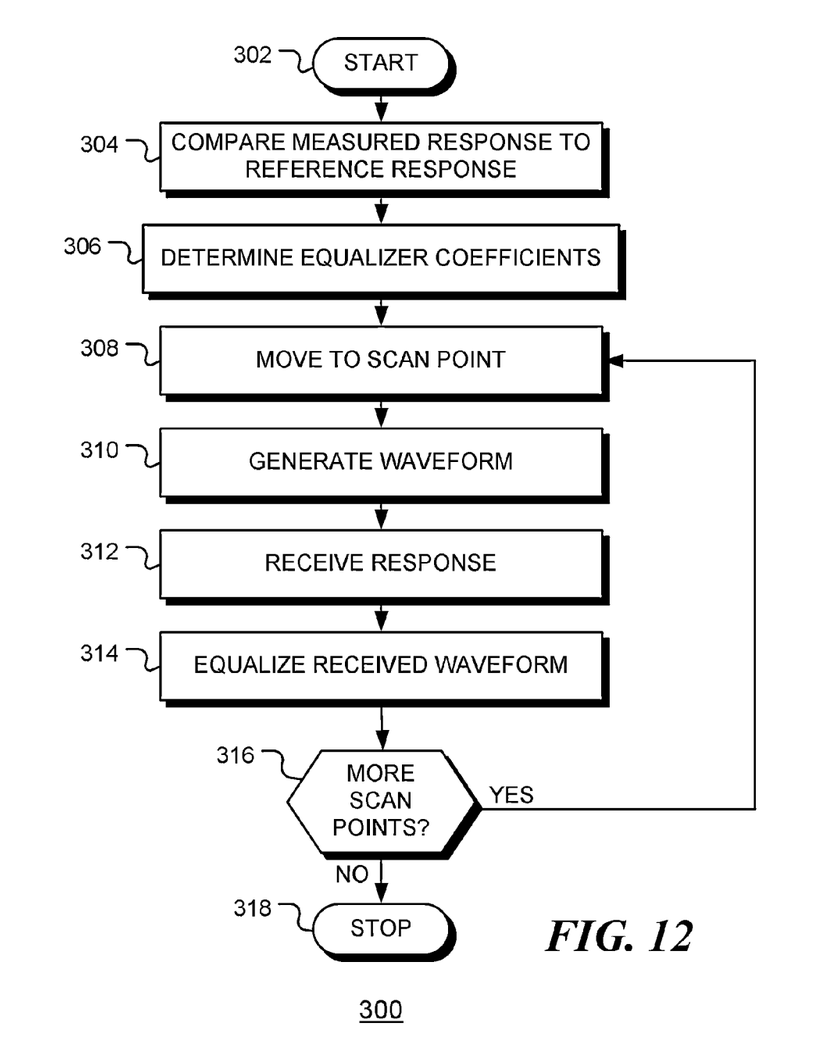
FIG. 12 is a flow chart of a method performing an ultrasound scan of an object, in accordance with some embodiments of the invention.

FIG. 12 is a flow chart 300 of a method of performing an ultrasonic scan of an object. Following start block 302, one or more measured responses from a signal path are compared to a reference response at block 304 and a set of equalizer coefficients are determined from these responses at block 306. These blocks do not need to be repeated for each scan, but may be repeated if any component of the signal path is changed. For example, the blocks may be repeated if a transducer in the path is replaced and a different transducer is used. If the signal path is substantially linear, then individual components in the path may be measured separately and their responses combined. At block 308, the scanning process begins and the transducers are moved to the first location on the scan path. An excitation waveform is generated at block 310, the response to the excitation waveform is received at block 312 and the received waveform is equalized at block 314. The equalized waveform may then be processed to form a point or pixel in the final image. If more points are to be imaged, as indicated by the positive branch from decision block 316, flow returns to block 308. If the scan is completed, as indicated by the negative branch from decision block 316, the scan terminates at block 318.

Figure 13:
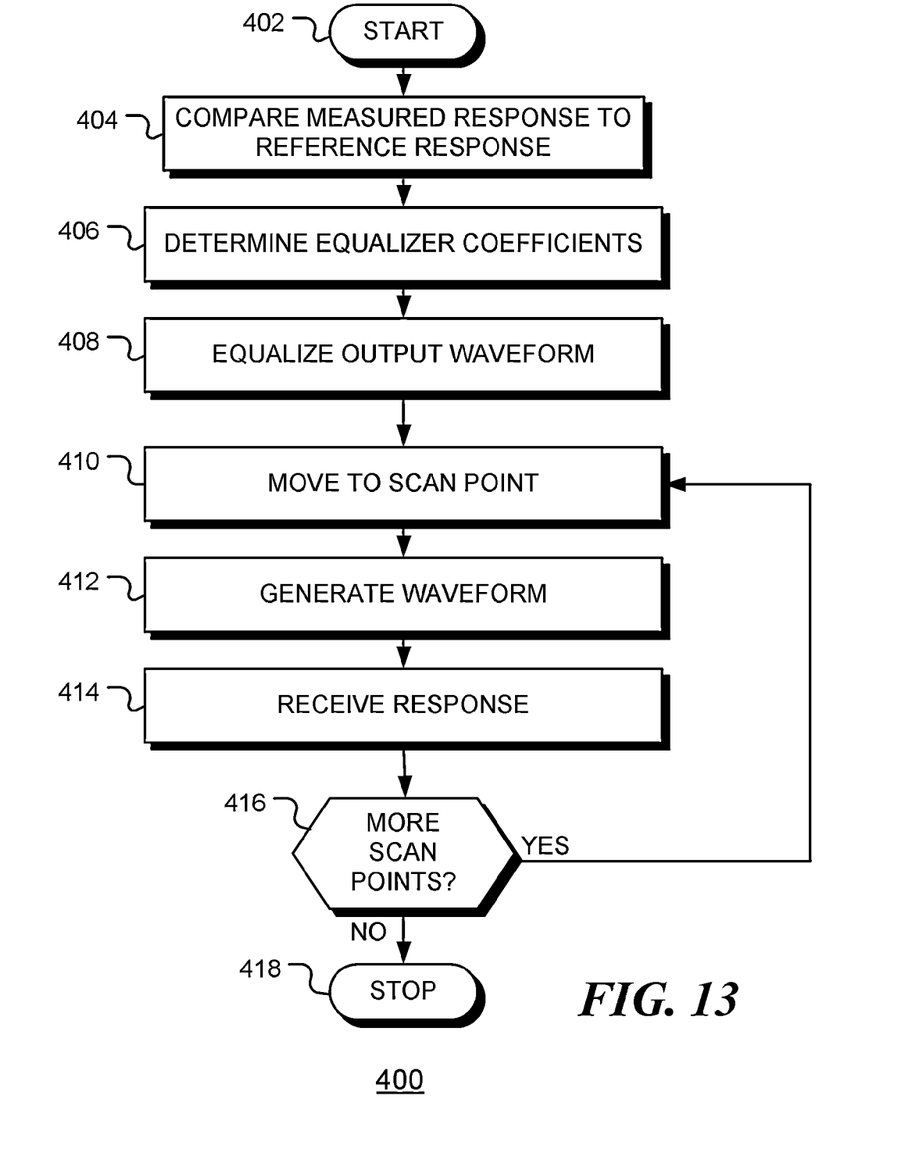
FIG. 13 is a flow chart of a further method for performing an ultrasound scan of an object, in accordance with some embodiments of the invention.

FIG. 13 is a flow chart 400 of a further method for performing an ultrasonic scan of an object. Following start block 402, one or more measured responses from a signal path are compared to the reference response at block 404 and a set of equalizer coefficients are determined from these responses at block 406. At block 408, an output waveform is equalized to obtain output waveforms for each signal path to be equalized. These blocks do not need to be repeated for each scan, but may be repeated if any component of the signal path is changed, or if a different output waveform is to be used. For example, the blocks may be repeated if a transducer in the path is replaced and a different transducer is used. At block 410 the scanning process begins and the transducers are moved to the first location on the scan path. An excitation waveform is generated at block 412 and the response to the excitation waveform is received at block 414. The response may then be processed to form a point or pixel in the final image. If more points are to be imaged, flow returns to block 410, as indicated by the positive branch from decision block 416. If the scan is completed, as indicated by the negative branch from decision block 416, the scan terminates at block 418.

As discussed above, one embodiment of a scanning acoustic microscope comprises a signal processor and a plurality of signal paths. Each signal path is operable to couple an ultrasonic transducer of a plurality of ultrasonic transducers to the signal processor, and each signal path has a response characteristic that includes a response characteristic of the ultrasonic transducer. At least one first signal path of the plurality of signal paths includes a signal path equalizer responsive to a set of equalization coefficients. The equalization coefficients are selected such that the response characteristic of the at least one first signal path more closely matches a reference characteristic response. In addition, the signal processor is operable to process signals received from the plurality of signal paths to produce an ultrasonic scan image.

A memory may be used to store the set of equalization coefficients associated with the at least one first signal path. The memory may be associated with the equalizer, the signal processor, or both.

The set of equalization coefficients may comprise a frequency domain transfer function, a gain value, or a set of time domain filter coefficients, for example.

The signal equalizer may be implemented as a programmed processor that executes a program of instructions, or as a hardware filter external to the signal processor.

A signal path may include a time gate. The time gate may be placed before or after the signal path equalizer.

In one embodiment, the scanning acoustic microscope is a pulse-echo scanning acoustic microscope that includes ultrasonic transducers operable to both generate and receive ultrasound. In this embodiment, the characteristic response of the signal path includes both the generation and reception response characteristics of the ultrasonic transducer in the signal path.

In a further embodiment the scanning acoustic microscope has a signal path that includes both an ultrasonic transmitter and an ultrasonic receiver. In this case the characteristic response of the signal path includes the response characteristic of the ultrasonic transmitter and the response characteristic of the ultrasonic receiver.

The set of equalization coefficients may comprise simple gain values for each signal path, or may be more general coefficients such as a transfer function, impulse response or other filter coefficients. The equalizer may have a linear or non-linear response.

In operation, at each scan point, ultrasound is received at a plurality of ultrasonic transducers. The ultrasound is produced in response to one or more ultrasound pulses incident upon the object. Response signals from the ultrasound pulses are transmitted along a plurality of signal paths, each signal path including an ultrasonic transducer of the plurality of ultrasonic transducers. The response signals are then processed to produce the ultrasonic image.

The signal paths include equalizers that affect the response signals to compensate, at least partially, for differences between the response characteristic of the signal path and a reference response characteristic.

In one embodiment, equalization is achieved by determining spectral components of the first response signal, scaling the spectral components by transfer function values to obtain scaled spectral components and determining an equalized first response signal from the scaled spectral components.

In a further embodiment, equalization is achieved by passing the first response signal through a time domain filter, such as a finite impulse response or recursive sampled data filter.

In operation, the ultrasonic transducers are spaced apart from one another, so as to scan different parts of an object (or different objects held in an object holder) and are moved together in a scan path between the scan points such that the spacing between ultrasonic transducers is maintained.

In still further embodiment, an equalized excitation waveform is generated for each signal path by modifying a base waveform to compensate, at least partially, for differences between the response characteristic of the signal path and a reference response characteristic. The equalized excitation waveform is transmitted along the associated signal path of the plurality of signal paths to produce ultrasound pulses incident upon the object. Response signals from multiple scan points are processed to produce an ultrasonic image.

Current solutions offered by the multi-transducer technique have inherent deficiencies that occur due to the inherent variation from transducer to transducer. These variations can manifest as brightness differences across the SAM image, or mixed interface imaging if narrow gates are used. These image variations, in turn, can result in erroneous analysis results that impact the pass/fail results of the object or objects under test. Gain equalization technique can account for strength variations between transducers, but it cannot account for shape/phase variations in the A-scans from different transducers. As disclosed above, waveform equalization can compensate for both strength and shape/phase variations from transducer to transducer, resulting in combined images that look uniform and provide for more accurate analysis results.

In the example described above, a transfer function was obtained for each transducer by comparing that transducer's average waveform to the reference waveform of that model of transducer. Then, the transfer function for a given transducer was applied to the waveform obtained at every pixel position, and the resulting image obtained showed more uniformity. While this example demonstrated the capability of waveform equalization, it will be apparent to those of ordinary skill in the art that other implementations may be used. For example, a slightly modified approach would be to create a filter that could be applied to each waveform on the A/D board after digitization, resulting in real-time equalization. To reduce the complexity of the filter, such as the number of coefficients, a technique such as adaptive filtering may be applied. Alternatively, the excitation waveform for each signal path could be modified.

Nomenclature

A-scan ultrasonic time-domain data obtained at a particular coordinate
N Total number of transducers used
$A_{ASCANS\_1}$ A-scans obtained from Transducer 1
$A_{ASCANS\_2}$ A-scans obtained from Transducer 2
$A_{ASCANS\_3}$ A-scans obtained from Transducer 3
$A_{ASCANS\_N}$ A-scans obtained from Transducer N
$H_{TF\_1}$ Transfer function obtained for Transducer 1
$H_{TF\_2}$ Transfer function obtained for Transducer 2
$H_{TF\_3}$ Transfer function obtained for Transducer 3
$H_{TF\_N}$ Transfer function obtained for Transducer N In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A scanning acoustic microscope comprising:
   a signal processor configured to couple to two or more ultrasonic transducers;
   a first signal path configured to couple first and second ultrasonic transducers of the two or more ultrasonic transducers to the signal processor, the first signal path comprising a first signal path equalizer configured to adjust a strength of a waveform from the first signal path and at least one of a shape and a phase of the waveform, and
   a coefficient memory coupled to the first signal path equalizer, the coefficient memory configured to store a first set of equalization coefficients associated with the first ultrasonic transducer and a second set of equalization coefficients associated with the second ultrasonic transducer;
   where, when the first signal path couples the first ultrasonic transducer to the processor, the first signal path equalizer is configured by the first set of equalization coefficients, such that the first signal path equalizer compensates, at least partially, for differences between the response characteristic of the first ultrasonic transducer and a reference transducer response, and where the first set of equalization coefficients are selected such that a waveform from the first ultrasonic transducer more closely matches a waveform from a reference transducer in both strength and shape or in both strength and phase, and
   where, when the first signal path couples the second ultrasonic transducer to the processor, the first signal path equalizer is configured by the second set of equalization coefficients, such that the first signal path equalizer compensates, at least partially, for differences between the response characteristic of the second ultrasonic transducer and the reference transducer response, and where the second set of equalization coefficients are selected such that a waveform from the second ultrasonic transducer more closely matches a waveform from the reference transducer in both strength and shape or in both strength and phase.

2. A scanning acoustic microscope in accordance with claim 1, wherein the first signal couples to the first ultrasonic transducer during a first time period, and couples to the second ultrasonic transducer during a second time period.

3. A scanning acoustic microscope in accordance with claim 1 further comprising:
a second signal path,
wherein during a first time period the first signal path couples to the first ultrasonic transducer and second signal path couples to the second ultrasonic transducer.

4. A scanning acoustic microscope in accordance with claim 1, wherein the reference transducer response is determined dependent upon the response characteristics of a plurality of ultrasonic transducers.

5. A scanning acoustic microscope in accordance with claim 1, wherein the reference transducer response comprises an average of the response characteristics of a plurality of ultrasonic transducers from a plurality of scans.

6. A scanning acoustic microscope in accordance with claim 3, wherein the second signal path comprises a second signal path equalizer and wherein the second signal path equalizer is configured by the second set of equalizer coefficients, such that the second signal path equalizer compensates, at least partially, for differences between the response characteristic of the second ultrasonic transducer and the reference transducer response.

7. A scanning acoustic microscope in accordance with claim 1, wherein at least the first set of equalization coefficients comprises a frequency domain transfer function.

8. A scanning acoustic microscope in accordance with claim 1, wherein at least the first set of equalization coefficients comprises a set of coefficients for a time domain filter, wherein the first signal path equalizer is held constant during operation of the scanning acoustic microscope.

9. A scanning acoustic microscope in accordance with claim 1, wherein the first signal path equalizer comprises a programmed processor operable to execute a program of instructions.

10. A scanning acoustic microscope in accordance with claim 1, wherein the first signal path equalizer comprises a hardware filter external to the signal processor.

11. A scanning acoustic microscope in accordance with claim 1, wherein the first signal path comprises a receiver, an amplifier and an analog-to-digital converter and wherein the signal processor comprises a digital signal processor.

12. A scanning acoustic microscope in accordance with claim 11, wherein the first signal path further comprises a pulse generator.

13. A scanning acoustic microscope in accordance with claim 11, wherein the first signal path equalizer is in the first signal path before the analog-to-digital converter.

14. A scanning acoustic microscope in accordance with claim 11, wherein the first signal path equalizer is in the first signal path after the analog-to-digital converter.

15. A scanning acoustic microscope in accordance with claim 1, wherein the first signal path comprises a time gate operable to receive signals from the signal path equalizer.

16. A scanning acoustic microscope in accordance with claim 1, wherein the first signal path comprises a time gate operable to pass signals to the first signal path equalizer.

17. A scanning acoustic microscope in accordance with claim 1,
wherein the scanning acoustic microscope comprises a pulse-echo scanning acoustic microscope,
the first and second ultrasonic transducers are operable to generate and receive ultrasound, and
the response characteristic of the first ultrasonic transducer comprises both the generation and reception response characteristics of the first ultrasonic transducer, and
the response characteristic of the second ultrasonic transducer comprises both the generation and reception response characteristics of the second ultrasonic transducer.

18. A scanning acoustic microscope in accordance with claim 1,
wherein the first ultrasonic transducer comprises an ultrasonic transmitter and the second ultrasonic transducer comprises an ultrasonic receiver,
wherein the first signal path comprises a transmission path that couples the first ultrasonic transducer to the signal processor and a reception path that couples the second ultrasonic transducer to the signal processor and wherein the characteristic response of the signal path comprises the response characteristic of the ultrasonic transmitter and the response characteristic of the ultrasonic receiver, and
wherein the first signal path equalizer is configured by a third set of equalization coefficients, such that the first signal path equalizer compensates, at least partially, for differences between the response characteristic of the first and second ultrasonic transducer and the reference transducer response.

19. A scanning acoustic microscope in accordance with claim 1, further comprising one or more second signal paths, each second signal path comprising a second signal path equalizer responsive to a set of equalization coefficients, stored in the coefficient memory, that are dependent upon the response characteristic of an ultrasonic transducer coupled to the signal processor via the second signal path.

20. A method for performing an ultrasonic scan of an object using
two or more ultrasonic transducers, the method comprising:
at each of a plurality of scan points, in response to an ultrasound pulse incident upon the object:
receiving a first response waveform from a first ultrasonic transducer of the two or more ultrasonic transducers, the first response waveform related to the incident ultrasound pulse by a first transducer response characteristic;
receiving a second response waveform from a second ultrasonic transducer of the two or more ultrasonic transducers, the second response waveform related to the incident ultrasound pulse by a second transducer response characteristic;
transmitting the first response waveform along a first signal path that couples the first ultrasonic transducer to a signal processor;
transmitting the second response waveform along a second signal path that couples the second ultrasonic transducer to the signal processor; and
processing, in the signal processor, the first and second response waveforms from each of the plurality of scan points to produce the ultrasonic image,
where transmitting the first response waveform along the first signal path comprises compensating the strength and at least one of the shape and phase of the first response waveform in a first signal path equalizer, to compensate, at least partially, for differences between the transducer response characteristic of the first ultrasonic transducer and a reference transducer response, such that the first response waveform more closely matches a waveform from a reference transducer, and
where transmitting the second response waveform along the second signal path comprises equalizing the second response waveform in a second signal path equalizer, to compensate, at least partially, for differences between the transducer response characteristic of the second ultrasonic transducer and the reference transducer response, such that the second response waveform more closely matches a waveform from the reference transducer.

21. A method in accordance with claim 20, wherein equalizing the first response signal comprises:
   determining frequency domain spectral components of the first response signal;
   scaling the spectral components by transfer function values to obtain scaled spectral components; and
   generating an equalized first response signal from the scaled spectral components.

22. A method in accordance with claim 21, wherein equalizing the first response signal comprises passing the first response signal through a time domain filter, wherein the characteristic of the time domain filter is held constant during the ultrasonic scan.

23. A method in accordance with claim 22, wherein the time domain filter comprises a sampled data filter.

24. A method in accordance with claim 20, further comprising:
   holding the first and second ultrasonic transducers spaced apart from one another; and
   moving the first and second ultrasonic transducers together in a scan path between the plurality of scan points such that the spacing between the first and second ultrasonic transducers is maintained.

25. A method in accordance with claim 20, further comprising:
   measuring responses from one or more ultrasonic transducers; and
   combining the responses to produce a reference transducer response,
wherein equalizing the first response signal produces an equalized response that substantially matches the reference transducer response.

26. A method in accordance with claim 20, further comprising:
   measuring one or more responses along the first signal path; and
   determining a relationship between the one or more responses and the reference transducer response,
wherein equalizing the first response signal, to substantially compensate for differences between the response of the first signal path and the reference transducer response, is dependent upon the relationship between the one or more responses and the reference transducer response.

27. A method in accordance with claim 20, further comprising:
   at each of a plurality of scan points:
      generating the ultrasound pulse incident upon the object from the first and second ultrasonic transducers.

28. A method in accordance with claim 20, further comprising:
   at each of a plurality of scan points:
      generating the ultrasound pulse incident upon the object from one or more further ultrasonic transducers.

29. A method for performing an ultrasonic scan of an object using scanning acoustic microscope, the method comprising:
   coupling a first ultrasonic transducer of two of more ultrasonic transducers to a signal processor of the scanning acoustic microscope along a first signal path;
   retrieving a first set of equalization coefficients, associated with the first ultrasonic transducer, from a coefficient memory that contains sets of equalization coefficients associated with each of the two or more ultrasonic transducers;
   compensating the strength and shape of an excitation waveform, dependent upon the first set of equalization coefficients, to produce an equalized excitation waveform, where the first set of equalization coefficients are selected such that an ultrasound waveform generated from the first ultrasonic transducer more closely matches an ultrasound waveform from a reference transducer in both strength and shape;
   at each of a plurality of scan points:
      transmitting the equalized excitation waveform along the first signal path of the plurality of signal paths to produce ultrasound pulses incident upon the object; and
      receiving ultrasound, produced in response to the ultrasound pulses to produce a plurality of response signals; and
   processing the plurality of response signals from the plurality of scan points to produce the ultrasonic image.

30. A scanning acoustic microscope comprising:
   a signal processor;
   a signal path configured to couple any selected ultrasonic transducer of a plurality of ultrasonic transducers to the signal processor, the signal path having a response characteristic that comprises a response characteristic of the selected ultrasonic transducer;
   a coefficient memory configured to store a set of one or more equalization coefficients for each of the plurality of ultrasonic transducers; and
   a signal path equalizer, in the signal path and coupled to the coefficient memory, the signal path equalizer configured by a set of one or more equalization coefficients of the selected ultrasonic transducer retrieved from the coefficient memory and the signal path equalizer configured to adjust the strength of a waveform from the selected ultrasonic transducer and at least one of the shape and phase of the waveform;
where the signal processor is operable to process signals received from the signal path to produce an ultrasonic scan image, and
where the set of one or more equalization coefficients of the selected ultrasonic transducer are determined, dependent upon a transducer response characteristic of the selected ultrasonic transducer, such that the response characteristic of the signal path, including the selected ultrasonic transducer, more closely matches a reference transducer response characteristic in strength and shape, in strength and phase, or in strength, shape and phase.

31. A scanning acoustic microscope in accordance with claim 1, wherein the first ultrasonic transducer is configured to generate ultrasound in response to an excitation waveform transmitted along the first signal.

32. A scanning acoustic microscope in accordance with claim 30, where the coefficient memory comprises a remote memory, the scanning acoustic microscope further comprising:
   a network interface operable to link the scanning acoustic microscope, via a network, to the remote memory.

33. A scanning acoustic microscope in accordance with claim 1, wherein the first ultrasonic transducer is configured to receive ultrasound and, in response, produces a response signal that is transmitted along the first signal path.

34. A scanning acoustic microscope in accordance with claim 1, wherein the first ultrasonic transducer is configured to both generate and receive ultrasound, wherein the first signal path includes a transmission path and a reception path and wherein the first signal equalizer is in the transmission path or the reception path.

35. A scanning acoustic microscope in accordance with claim 1, wherein configuration of the first signal path equalizer is held constant during operation of the scanning acoustic microscope.

36. A scanning acoustic microscope comprising:
   a signal processor configured to couple to two or more ultrasonic transducers having non-identical response characteristics;
   a first equalizer in a first signal path that couples a first ultrasonic transducer of the two or more ultrasonic transducers to the signal processor, the first equalizer configured by a first set of equalization coefficients associated with the first ultrasonic transducer to adjust a strength of a waveform from the first ultrasonic transducer and at least one of a shape and a phase of the waveform; and
   a second equalizer in a second signal path that couples a second ultrasonic transducer of the two or more ultrasonic transducers to the signal processor, the second equalizer configured by a second set of equalization coefficients associated with the second ultrasonic transducer to adjust a strength of a waveform from the second ultrasonic transducer and at least one of a shape and a phase of the waveform; and
wherein the first equalization coefficients are selected, such that the waveform from the first ultrasonic transducer more closely matches a waveform from a reference transducer in strength and shape, in strength and phase, or in strength, shape and phase and
wherein the second equalization coefficients are selected, such that the waveform from the second ultrasonic transducer more closely matches a waveform from the reference transducer in strength and shape, in strength and phase, or in strength, shape and phase.

37. A scanning acoustic microscope comprising:
   a signal processor configured to couple to an ultrasonic transducer selected from a set of two or more ultrasonic transducers having non-identical response characteristics;
   a coefficient memory configured to store sets of equalization coefficients associated with the two or more ultrasonic transducers; and
   a waveform equalizer in a signal path that couples the selected ultrasonic transducer of the set of ultrasonic transducers to the signal processor, the waveform equalizer configured by a set of equalization coefficients retrieved from the coefficient memory and associated with the selected ultrasonic transducer;
wherein the waveform equalizer adjusts a strength of a waveform from the selected ultrasonic transducer and at least one of a shape and a phase of the waveform;
wherein the set of equalization coefficients associated with the selected ultrasonic transducer are determined such that the waveform from the selected ultrasonic transducer more closely matches a waveform from a reference transducer in strength and shape, in strength and phase, or in strength, shape and phase, so that the waveform equalizer compensates, at least partially, for differences between the response characteristic of the selected ultrasonic transducer and a reference transducer response.

* * * * *